(12) United States Patent
Haery (10) Patent No.: US 10,029,077 B2
(45) Date of Patent: *Jul. 24, 2018

(54) APPARATUS AND PROCESSES FOR APPLYING SUBSTANCES WITHIN MAMMALIAN TISSUE

(71) Applicant: Cameron Haery, Highland Park, IL (US)

(72) Inventor: Cameron Haery, Highland Park, IL (US)

( * ) Notice: Subject to any disclaimer, the term of this patent is extended or adjusted under 35 U.S.C. 154(b) by 497 days.

This patent is subject to a terminal disclaimer.

(21) Appl. No.: 14/826,337

(22) Filed: Aug. 14, 2015

(65) Prior Publication Data

US 2015/0352334 A1   Dec. 10, 2015

Related U.S. Application Data

(63) Continuation of application No. 12/906,671, filed on Oct. 18, 2010, now Pat. No. 9,119,943.

(51) Int. Cl.
| | |
|---|---|
| *A61M 25/10* | (2013.01) |
| *A61M 25/09* | (2006.01) |
| *A61M 31/00* | (2006.01) |
| *A61L 31/14* | (2006.01) |

(52) U.S. Cl.
CPC ....... *A61M 25/1002* (2013.01); *A61L 31/146* (2013.01); *A61M 25/09* (2013.01); *A61M 25/104* (2013.01); *A61M 2025/09175* (2013.01); *A61M 2025/105* (2013.01); *A61M 2025/1047* (2013.01); *A61M 2025/1084* (2013.01);

(Continued)

(58) Field of Classification Search
CPC .............. A61M 25/09; A61M 25/1002; A61M 25/104; A61M 2025/09175; A61M 2025/1047; A61M 2025/105; A61M 2025/1084; A61M 2025/1097; A61M 2025/1088; A61M 2025/1086

See application file for complete search history.

(56) References Cited

U.S. PATENT DOCUMENTS

| | | |
|---|---|---|
| 5,000,734 A | 3/1991 | Boussignac et al. |
| 5,232,444 A | 8/1993 | Just et al. |
| 5,313,967 A | 5/1994 | Lieber et al. |

(Continued)

FOREIGN PATENT DOCUMENTS

| | | |
|---|---|---|
| JP | H02-502975 | 9/1990 |
| JP | H03505411 | 11/1991 |

(Continued)

OTHER PUBLICATIONS

Y. Krishnamachari et al., "PLGA Microparticle Based Vaccine Carriers for Tumor Immunotherapy" University of Iowa, XP-002670681, Abstract.

(Continued)

*Primary Examiner* — Matthew F Desanto
(74) *Attorney, Agent, or Firm* — Klintworth & Rozenblat IP LLP (57) ABSTRACT

An apparatus for applying a substance to internal mammalian tissue is provided. The apparatus includes a member having a flexible, absorbent, porous portion connected to a non-porous portion. The apparatus may be used to treat atrial fibrillation or other non-atrial fibrillation issues with internal mammalian tissue.

29 Claims, 11 Drawing Sheets

(52) U.S. Cl.
CPC ............... *A61M 2025/1086* (2013.01); *A61M 2025/1088* (2013.01); *A61M 2025/1097* (2013.01)

(56) References Cited

U.S. PATENT DOCUMENTS

| | | | |
|---|---|---|---|
| 5,706,827 A | 1/1998 | Ehr et al. | |
| 6,050,930 A | 4/2000 | Teirstein | |
| 6,146,401 A | 11/2000 | Yoon et al. | |
| 6,267,747 B1 | 7/2001 | Samson et al. | |
| 6,364,856 B1 | 4/2002 | Ding et al. | |
| 6,529,756 B1 | 3/2003 | Phan et al. | |
| 6,689,119 B1 | 2/2004 | Di Caprio et al. | |
| 9,119,943 B2 * | 9/2015 | Haery | A61M 25/09 |
| 2001/0039445 A1 | 11/2001 | Hall et al. | |
| 2005/0043678 A1 | 2/2005 | Freyman et al. | |
| 2008/0140002 A1 | 6/2008 | Ramzipoor et al. | |

FOREIGN PATENT DOCUMENTS

| | | |
|---|---|---|
| JP | 2003500121 | 1/2003 |
| JP | 2006-518648 | 8/2006 |
| JP | 2009534094 | 9/2009 |
| JP | 2010521264 | 6/2010 |
| WO | 200193939 A1 | 12/2001 |
| WO | 2004/073505 A2 | 9/2004 |
| WO | 2008/113857 A2 | 9/2008 |
| WO | 2011110290 A1 | 9/2011 |

OTHER PUBLICATIONS

A. Salem, "BIOT 436 Biodegradable microparticle delivery antigens and adjuvants stimulate potent anti-tumor antigen-specific immune responses" XP-002670680, http://oasys2.confex.com/acs/232nm/techprogram/P968799. DHTML, p. 1, Feb. 29, 2012.

M. Singh et al., "Nanoparticles and microparticles as vaccine-delivery systems" XP009119477, www.future-drugs.com, ISSN 1476-0584, 10.1586/14760584.6.5.797, pp. 797-808,2007.

* cited by examiner

FIG. 10

APPARATUS AND PROCESSES FOR APPLYING SUBSTANCES WITHIN MAMMALIAN TISSUE

RELATED APPLICATIONS

The present application is a continuation of co-pending U.S. patent application Ser. No. 12/906,671, filed Oct. 18, 2010, the content of which is incorporated by reference herein in its entirety.

FIELD OF THE DISCLOSURE

The disclosure relates to apparatus and processes for applying substances within mammalian tissue to chemically treat atrial fibrillation, or to chemically treat other types of non-atrial fibrillation issues involving internal mammalian tissue.

BACKGROUND OF THE DISCLOSURE

Atrial fibrillation is one of the most common arrhythmias in the world and is recognized as one of the most serious medical epidemics. Atrial fibrillation is a leading cause of stroke, thromboembolism, mortality, and debilitation. Common debilitating symptoms of atrial fibrillation include but are not limited to palpitations, dyspnea, dizziness, chest pain, weakness, and long term debility associated with stroke and congestive heart failure. There is a large economic burden to society associated with atrial fibrillation including: medical care costs resulting from medical therapy, symptom relief, hospitalizations, and invasive procedure and device therapy; lost time from the workforce; and long term care costs associated with morbidity of stroke, heart failure, and debilitation.

The current drug-related therapies for atrial fibrillation require relatively high doses of drugs systemically to effect the substrate tissue in the atrium in order to have any positive effect. However, these drugs have serious side effects, and are largely inadequate. One therapy for atrial fibrillation comprises ventricular rate control drugs. However, common side effects of this therapy include bradycardia, weakness, low energy levels, and other side effects. Moreover, this treatment may require pacemaker implantation which is invasive and costly. Another adjunctive therapy for atrial fibrillation comprises blood thinners. However, blood thinners have significant side effects and may lead to minor and catastrophic bleeding complications, may require frequent blood tests, and may have a narrow and difficult to achieve therapeutic window to achieve therapeutic blood levels. Still another therapy for atrial fibrillation comprises antiarrhtyhmic drugs. However, antiarrhtyhmic drugs have a limited effectiveness in maintaining normal heart rhythm, and have a wide range of toxic systemic side effects. Moreover, antiarrhtyhmic drugs may induce pro-arrhythmia, and have negative drug interactions with other medications.

The current procedural therapies for atrial fibrillation are also largely inadequate. One procedure for atrial fibrillation comprises electrical cardioversion. This procedure requires sedation or general anesthesia. Moreover, atrial fibrillation commonly reoccurs after electrical cardioversion. Another procedure for atrial fibrillation comprises invasive catheter ablation such as: radiofrequency ablation; cryothermy; ultrasound ablation; laser ablation; or electrical ablation. Catheter ablation is intended to ablate arrhythmogenic cells in or around the left atrium. The majority of cases are known to originate from the endocardium or myocardium within or around the pulmonary veins. Creating circumferential ablation lesions around pulmonary veins is intended to cause electrical isolation of the abnormal cells within the pulmonary veins, rending these trigger zones unable to propagate abnormal electrical impulses into the left atrium, making them incapable of causing atrial fibrillation. Pulmonary vein ablation for atrial fibrillation remains a promising therapy, but has proven to be each of the following: limited in efficacy; have risks and complications associated with an invasive procedure; require specialized skill and training leading to higher costs, and a lower number of patients that can be treated due to the lack of operators with this specialized training; require a long procedure time to effectively map, through electrophysiology mapping, specific trigger zones around the pulmonary vein ostia prior to delivering the catheter based injury; and often require repeat procedures for a successful outcome. Moreover, current catheter ablation techniques are limited in their success in part due to the inability to deliver the ablative injury to all substrate tissue that causes atrial fibrillation. This limitation may leave potential gaps in the target area of ablation that is not treated. This is often caused due to limitations in controlling the catheter tip and the inability to provide multiple burns at the end of the catheter in the same spot due to the risk of perforation. Frequently, patients are required to return for multiple repeat procedures in attempts to ablate missed areas. Current catheter-based therapies are hampered by their inability to consistently, effectively, and predictably create circumferential, continuous, or curvilinear ablation lines to eradicate origins of irregular electrical activity, and to isolate the target tissue from further propagating abnormal electrical impulses. Serious complications related to current ablation therapies include: left atrial perforation leading to hemopericardium and cardiac tamponade; pulmonary vein stenosis; left atrial-espohageal fistula; thromboembolic events, such as stroke and myocardial infarction, resulting directly from injury created by current equipment and techniques, and other complications.

An apparatus and process is needed to effectively treat atrial fibrillation, or other types of non-atrial fibrillation issues involving mammalian tissue, while avoiding one or more of the side-effects associated with the current treatments.

SUMMARY OF THE DISCLOSURE

In one embodiment, an apparatus for applying a substance to internal mammalian tissue comprises a member having a flexible, absorbent, porous portion connected to a non-porous portion.

In another embodiment, a balloon-catheter for applying a substance to internal mammalian tissue comprises: an inflatable and deflate-able balloon comprising a flexible, absorbent, porous portion connected to a non-porous portion to form a cavity; and a catheter connected to the balloon.

In an additional embodiment, a guide-wire is provided having a portion for being magnetized, and another portion which is non-magnetic.

In an additional embodiment, a method of applying a substance to internal mammalian tissue is provided. In one step, a member is deployed within a mammal. In another step, a flexible, absorbent, porous portion of the member is disposed against internal tissue of the mammal. In an additional step, a substance, disposed in a cavity between the flexible, absorbent, porous portion of the member and a non-porous portion of the member, is infused through the flexible, absorbent, porous portion to contact the internal mammalian tissue.

These and other features, aspects and advantages of the disclosure will become better understood with reference to the following drawings, description and claims.

DETAILED DESCRIPTION OF THE DISCLOSURE

The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims.

Figure 1:
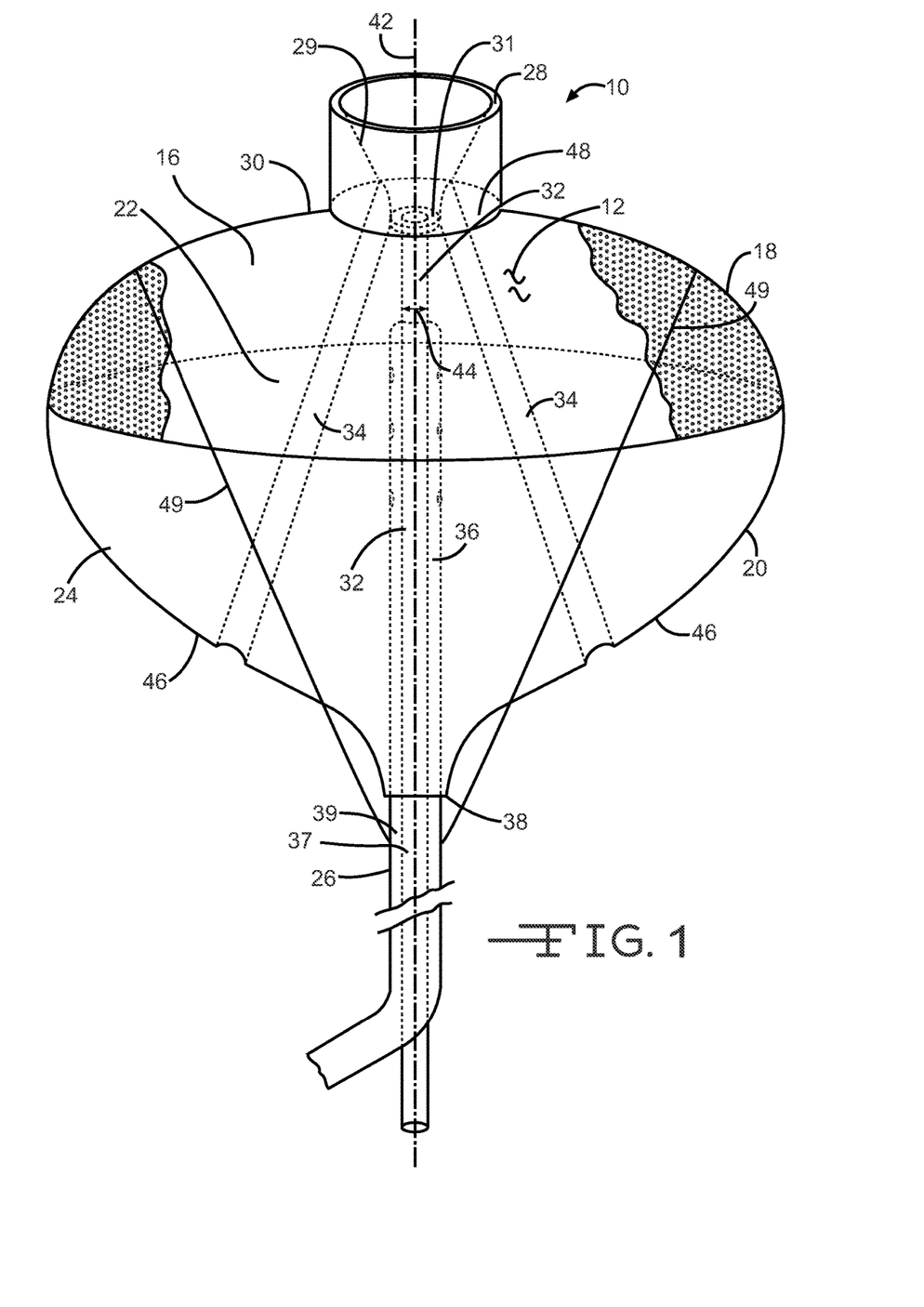
FIG. 1 illustrates a perspective view of one embodiment under the disclosure of an apparatus for applying a substance to internal mammalian tissue.
Figure 1A:
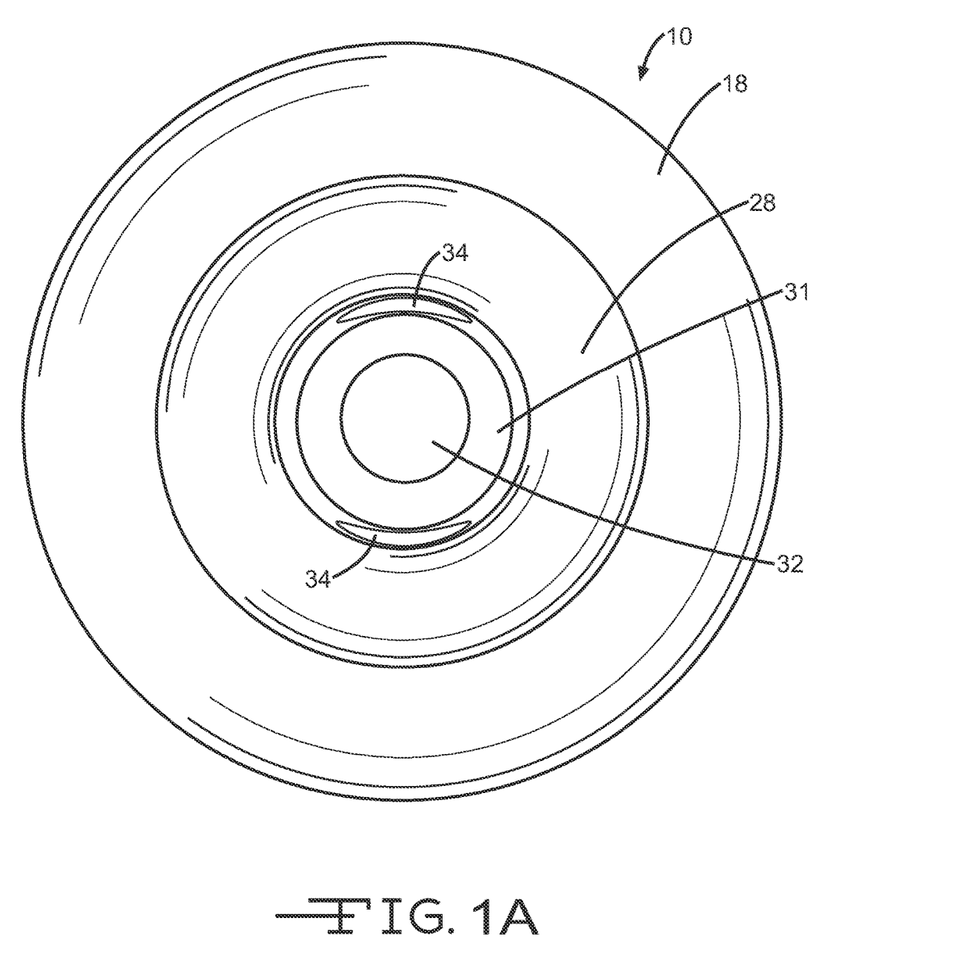
FIG. 1A illustrates a top view of the apparatus of FIG. 1.

FIGS. 1 and 1A illustrate one embodiment under the disclosure of an apparatus 10 for applying a substance 12 to internal mammalian tissue. For purposes of this disclosure, the term 'mammal' comprises a human-being or any type of animal. The apparatus 10 includes a member 16 having a flexible, absorbent, porous portion 18 connected to a non-porous portion 20. For purposes of this disclosure, the term 'flexible' means bending readily without breaking. For purposes of this disclosure, the term 'absorbent' means a material which has the capacity or tendency to absorb a substance. For purposes of this disclosure, the term 'non-porous' means not permeable to water, or other fluids. The member 16 may comprise a medical device. The flexible, absorbent, porousportion 18 is absorbent, is porous or partially porous, and will saturate or partially saturate with the substance 12 allowing the substance 12 to pass through the flexible, absorbent, porous portion 18. For purposes of this disclosure, the term 'porous' means a material having pores which allow fluids to pass through the material. The flexible, absorbent, porous portion 18 is sufficiently soft, malleable, and compliant, such that when gentle pressure is applied by an operator to press it against an endocardial surface during an atrial fibrillation treatment, or other medical treatment, the flexible absorbent portion 18 will compress and be in complete opposition to the endocardial surface filling the crevices of the endocardial surface regardless of any surface irregularities in endocardial surface topography. The apparatus 10 may be used to apply the substance 12 to any type of internal mammalian tissue. The flexible, absorbent, porous portion 18 may be made of any flexible, absorbent, saturating material such as foam, synthetic foam, foam rubber, natural sponge, synthetic sponge, synthetic rubber, or other materials that will absorb the substance 12 and will expand when saturated to fully adhere to the surface being treated. The non-porous portion 20 may be made of a standard cardiovascular angioplasty balloon material which is non-porous and non-absorbent which will not absorb or extrude the substance 12. The member 16 may comprise an inflatable and deflate-able cavity 22 formed between the flexible, absorbent, porous portion 18 and the non-porous portion 20. The member 16 may comprise a balloon-catheter comprising an inflatable and deflate-able balloon 24 connected to a catheter 26. The flexible, porous, absorbent portion 18 may comprise the top-half of the balloon 24, and the non-porous portion 20 may comprise the bottom-half of the balloon 24. In other embodiments, the flexible, absorbent, porous portion 18 and the non-porous portion 20 may vary in shape, size, orientation, configuration, or relation to one another. The member 16 may include a nipple 28 extending from a top end 30 of the flexible, absorbent, porous portion 18. A tapered hole 29 may extend through the nipple 28. The tapered hole 29 may end at a base surface 31 of the nipple 28. The member 16 may comprise first, second, and third lumens 32, 34, and 36. The catheter 26 may comprise first and second catheter lumens 37 and 39. The first lumen 32 may comprise an open-ended, through-lumen which extends continuously from and through the nipple 28 in the top end 30 of the flexible, absorbent, porous portion 18, through the cavity 22 of the member 16, to and through a bottom end 38 of the non-porous portion 20. The first lumen 32 may be aligned with the first catheter lumen 37 of the catheter 26 to form a continuous through-lumen. The first lumen 32 may extend along and through a long axis 42 of the member 16. The first lumen 32 may have a width 44. In other embodiments, there may be any number of first lumen 32 of varying shape, size, configuration, or orientation. The second lumen 34 may comprise two, spaced-apart, open-ended, through lumens which extend continuously from and through lateral surfaces 46 of the member 16, through the cavity 22 of the member 16, to and through the top end 30 of the member 16. The second lumen 34 may extend from the non-porous portion 20 of the member 16 through the nipple 28 of the top end 30 of the flexible, absorbent, porous portion 18 of the member 16. As shown in FIG. 1A, the second lumen 34 may be crescent-shaped. In other embodiments, there may be any number of second lumen 34 of varying shapes, sizes, configurations, or orientations. The third lumen 36 may comprise a closed-end lumen extending from the second catheter lumen 39 into the closed-end, inflatable and deflate-able cavity 22. In other embodiments, there may be any number of third lumen 36 of varying shape, size, configuration, or orientation. The member 16 may further comprise a ferromagnetic portion 48 which may be disposed in the nipple 28, in the base surface 31 of the nipple 28, or in any other portion of the member 16. In other embodiments, the ferromagnetic portion 48 may be disposed in varying portions of the member 16. The member 16 may optionally include one or more Nitinol runners 49 that are connected between the flexible, absorbent, porous portion 18 and the catheter 26. In other embodiments, the member 16, including all of its components, may be of a varying shape, size, configuration, or orientation.

Figure 2:
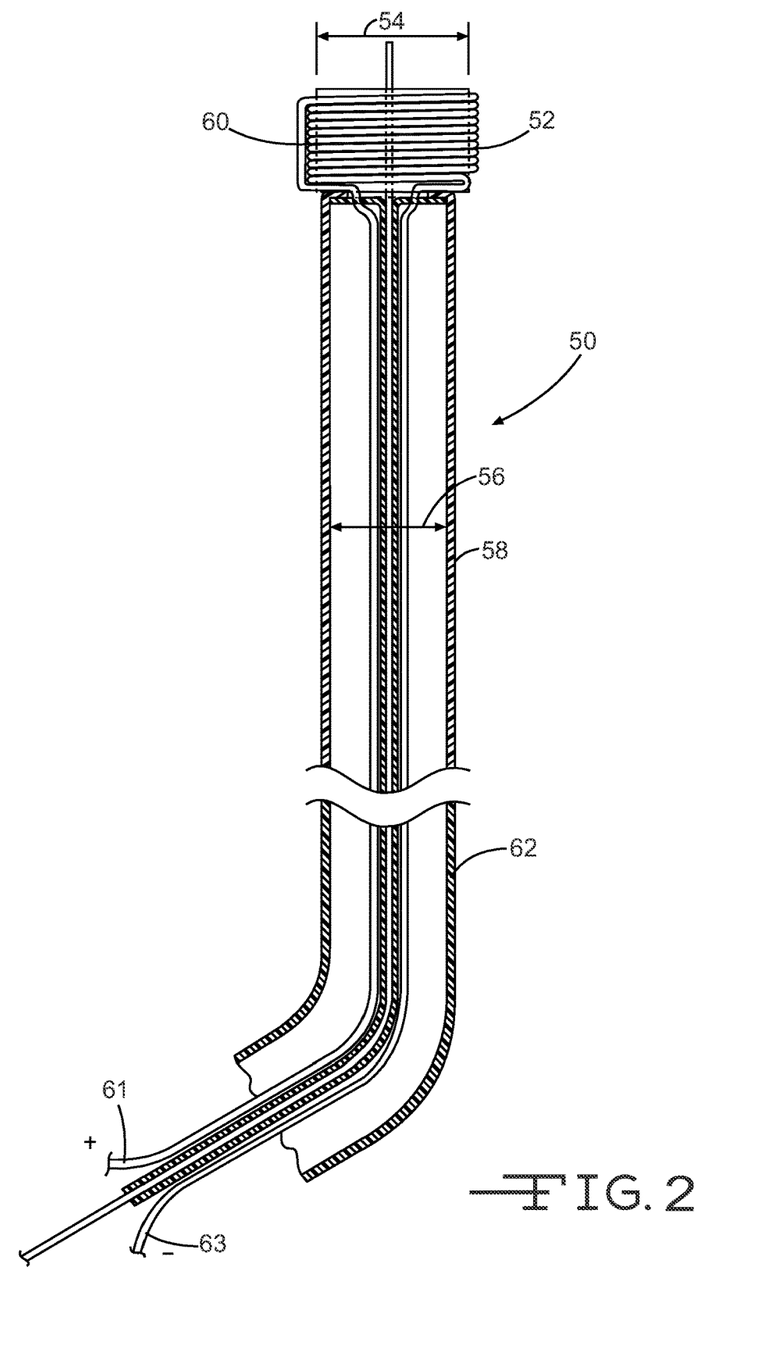
FIG. 2 illustrates one embodiment under the disclosure of a guide-wire.

FIG. 2 illustrates one embodiment under the disclosure of a guide-wire 50. The guide-wire may 50 have a diameter of 0.025 inches, 0.035 inches, or 0.038 inches. In other embodiments, the size of the guide-wire 50 may vary. The guide-wire 50 may have a stepped-up portion 52 which has a width 54 which is greater than widths 56 of other portions 58 of the guide-wire 50. The width 54 of the stepped-up portion 52 may also be greater than a width 44 of the first lumen 32 of the member 16 shown in FIGS. 1 and 1A. The guide-wire 50 may also have a portion 60 having an electromagnet or any other mechanism or material with magnetic capability for being magnetized by magnetic inducing apparatus known in the art. The portion 60 may comprise the stepped-up portion 52. In other embodiments, the portion 60 may be different than the stepped-up portion 52. The portion 60 for being magnetized may comprise a ferromagnetic core with a surrounding wire coil, helical arrangement, solenoid, corkscrew arrangement, or other configuration for being magnetized. When an electric current is applied to the magnetic portion 60, such as by hooking up ends 61 and 63 of the portion 60 to a device supplying positive and negative charges, an electromagnetic field will be created in order to attract or repulse the ferromagnetic portion 48 of the member 16 relative to the magnetic portion 60. In such manner, the magnetic portion 60 of the guide-wire 50 may be used to control precise movement of the member 16 when disposed within a pulmonary vein or other tissue of a mammal. The strength of the attraction or repulse may be controlled by the strength of the electrical current applied. When the electrical current is turned off, the magnetic field is eliminated allowing the guide-wire 50 to operate as a standard guide-wire. The guide-wire 50 may also have another portion 62 which is non-magnetic. Portion 62 may comprise an insulating, non-magnetic material covering most of portion 60. In one embodiment, portion 62 may cover the entire portion 60 with the exception of at the ends 61 and 63, and at the stepped-up portion 52. In other embodiments, the portion 62 may cover varying segments of portion 60 in varying shapes, sizes, orientations, or configurations.

Figure 3:
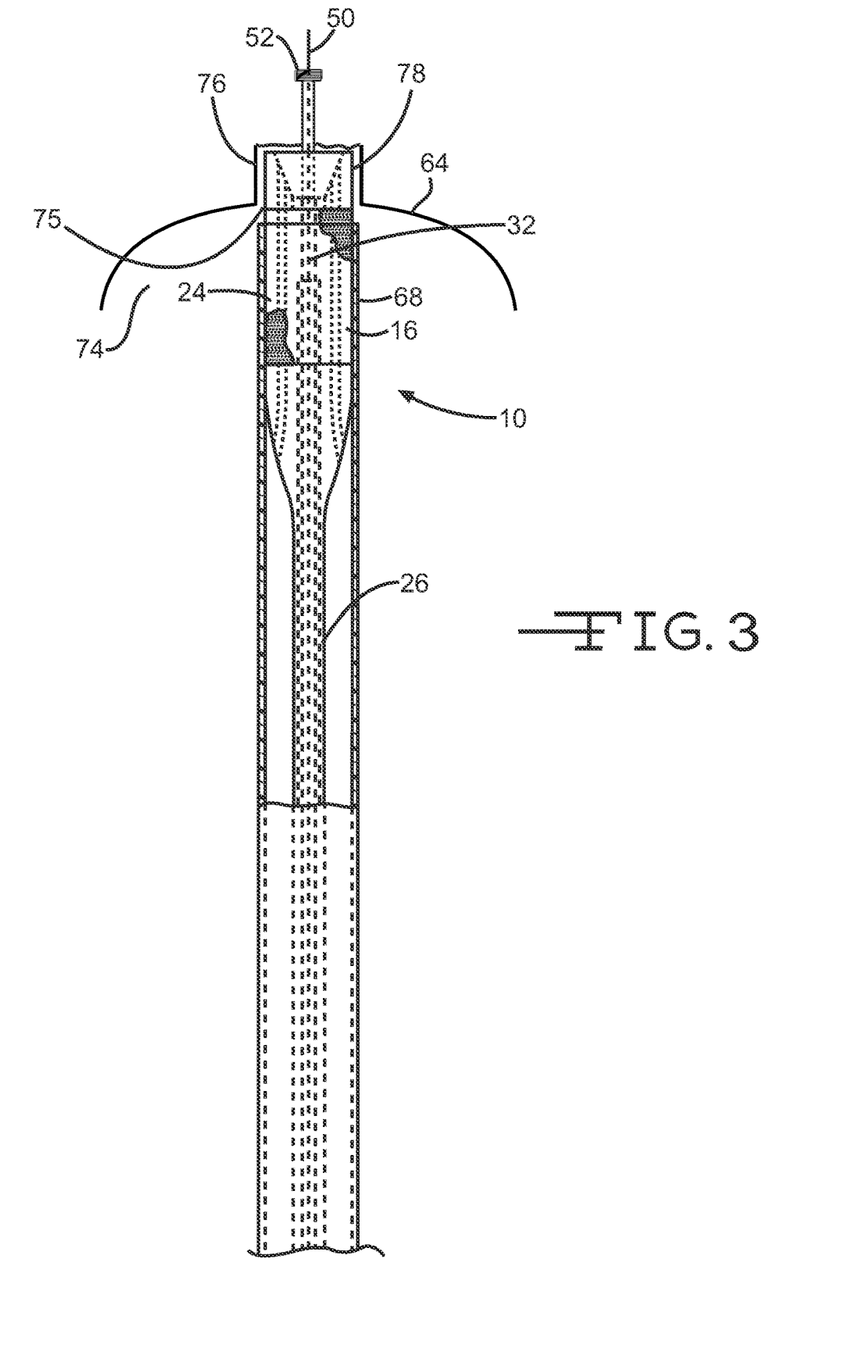
FIG. 3 illustrates a side view of the apparatus of FIG. 1 being deployed within a mammal over the guide-wire of FIG. 2 with the apparatus partially stowed within a sheath.

FIGS. 3-10 illustrate various steps of a method for the apparatus 10 being deployed in a mammal to apply a substance 12 to internal mammalian tissue 64. As illustrated in FIG. 3, the apparatus 10 may be deployed within the mammal. The apparatus 10 may comprise a member 16 comprising a balloon-catheter comprising an inflatable and deflate-able balloon 24 connected to the catheter 26. The member 16 may be deployed by inserting a guide-wire 50 from across an interatrial septum into a pulmonary vein 76 of the mammal, such as the left superior pulmonary vein, the left inferior pulmonary vein, the right superior pulmonary vein, or the right inferior pulmonary vein. A stepped-up portion 52 of the guide-wire 50 may be inserted into a hole 75 of the left atrium 74 and extended into a pulmonary vein ostium 78 of the pulmonary vein 76. The balloon 24 may be delivered towards the internal mammalian tissue 64, with the balloon 24 partially stowed in an unexpanded/deflated stated within a sheath 68, by following the first lumen 32 of the balloon 24 along the guide-wire 50 disposed in the pulmonary vein 76. In order to minimize the risk of thrombus formation on the member 16, the mammal may be adequately anticoagulated with systemic medications including but not limited to unfractionated heparin, warfarin, low-molecular weight heparin, direct-thrombin inhibitor, glycoprotein 2b/3a antagonists, aspirin, clopidogrel, prasugrel, thrombolytic agents, or other types of anticoagulation medications. During this process, the nipple 28 of the balloon 24 may be disposed outside of the sheath 68, with the remainder of the deflated balloon 24 disposed within the sheath 68. By pushing the sheath 68 or the catheter 26 towards the internal mammalian tissue 64, the nipple 28 of the balloon 24 may be extended into the hole 75 of the left atrium 74 and extended into the pulmonary vein ostium 78 of the pulmonary vein 76 to come to a resting location disposed apart from the stepped-up portion 52 of the guide-wire 50. The nipple 28 may be sized to fit snugly against the hole 75 of the left atrium 74 to assist in securing the balloon 24 in place.

Figure 4:
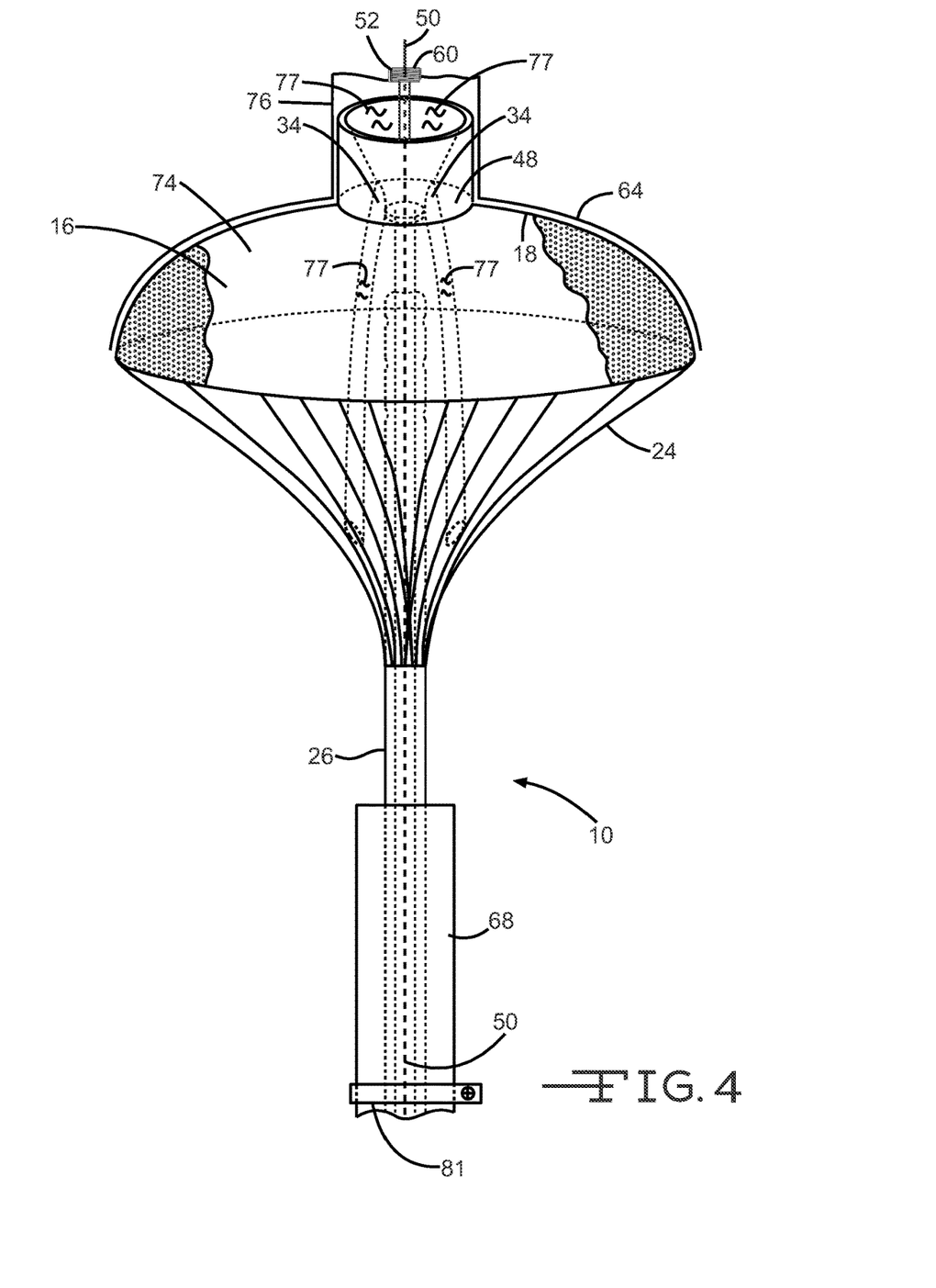
FIG. 4 illustrates a perspective view of the apparatus of FIG. 3 being extended out of the sheath within the mammal.

As illustrated in FIG. 4, during deployment the sheath 68 may be pulled away from the internal mammalian tissue 64 and the catheter 26 may be pushed towards the internal mammalian tissue 64 to move the remaining portion of the deflated balloon 24 outside the sheath 68 towards the internal mammalian tissue 64. In one embodiment, the internal mammalian tissue 64 to be treated may comprise pulmonary vein ostial tissue, pulmonary vein tissue 76, or an endocardial surface of the left atrium 74. During this process, the flexible, absorbent, porous portion 18 of the member 16 may pop-out of the sheath 68 and extend into its natural uncompressed state disposed against the internal mammalian tissue 64. The non-porous portion 24 of the member 16 may begin to un-crinkle as the flexible, absorbent, porous portion 18 extends. The flexible, absorbent, porous portion 18 may have a shape that will juxtapose, adhere, or make contact with the internal mammalian tissue 64, which may comprise pulmonary vein ostial tissue, pulmonary vein tissue 76, or the endocardial surface, of the left atrium 74. This shape may be circular, ovoid, elliptical or another shape. In one embodiment, the process may comprise an operator pushing the catheter 26 until the flexible, absorbent, porous portion 18 of the balloon 24 is disposed against the internal mammalian tissue 64, which may comprise the pulmonary vein ostial tissue, pulmonary vein tissue 76, or the endocardial surface, of the left atrium 74. In another embodiment, the process may comprise attracting and moving a ferromagnetic portion 48 of the balloon 24 towards a magnetized portion 60 of the guide-wire 50 to dispose the flexible, absorbent, porous portion 18 of the balloon 24 against the internal mammalian tissue 64, which may comprise the pulmonary vein ostial tissue, pulmonary vein tissue 76, or the endocardial surface, of the left atrium 74. Blood 77 may flow from the pulmonary vein 76 through the second lumen 34 of the balloon 24 into the left atrium 74. This may minimize or eliminate temporary reduction of blood flow from the pulmonary vein 76 into the left atrium 74 during use of the balloon 24. An attachment member 81, such as a clip or other type of attachment member, may be used in the embodiment in which the ferromagnetic portion 48 of the balloon 24 is attracted towards the magnetized portion 60 of the guide-wire 50. When the balloon 24 is located in the desired location relative to the tissue being treated, the attachment member 81 may be used to fixedly attach the guide-wire 50 to the sheath 68 to keep the balloon 24 and the guide-wire 50 at a fixed distance apart from one another during treatment. This will result in the magnetic field exerting a constant electromagnetic force between the magnetized portion 60 of the guide wire 50 and the ferromagnetic portion 48 of the balloon 24 keeping the balloon 24 in the desired location to treat the tissue for any desired period of time.

Figure 5:
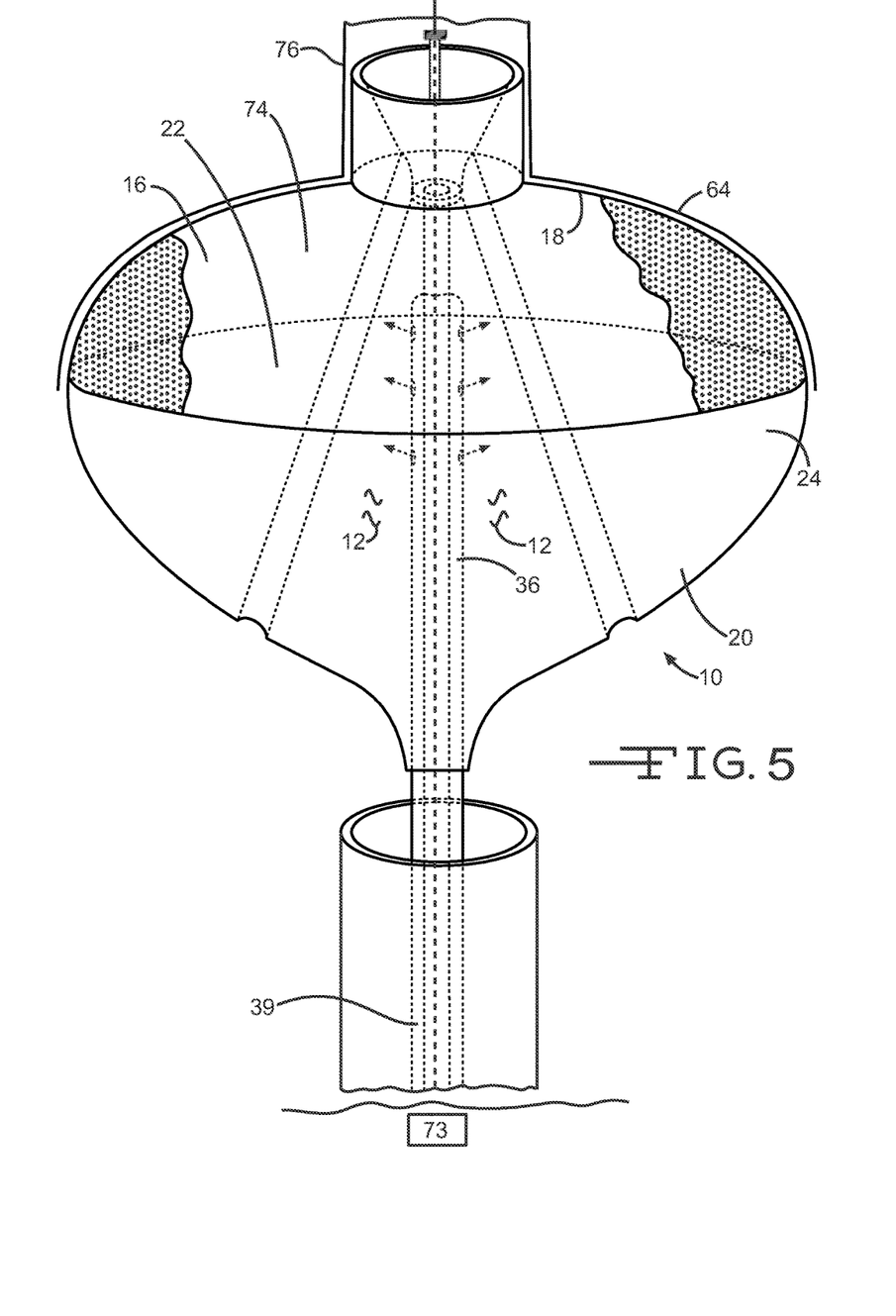
FIG. 5 illustrates the perspective view of the apparatus of FIG. 4 with the apparatus having been inflated.

As illustrated in FIG. 5, a substance 12 may be infused, using an infusion device 73, through the second catheter lumen 39, into the third lumen 36, and into the cavity 22 in order to inflate/expand the cavity 22 of the balloon 24 with the substance 12. The substance 12 may comprise any substance for altering physiologic properties of internal mammalian tissue 64, such as pulmonary vein ostial tissue, pulmonary vein tissue 76, or endocardial surface tissue, of the left atrium 74, or other types of mammalian tissue. The substance 12 may comprise any antiarrhythmic medication which is effective when applied topically, or any other drug that may have antiarrhythmic effects. The substance 12 may comprise drugs in CLASS 1, CLASS 2, CLASS 3, CLASS 4, or any other substance, currently known or discovered in the future, that affects tissue for the treatment of any type of health-related issue. The substance 12 may comprise any of the following: amiodarone, quinidine, disopyramide, lidocatine, procainamide, dofetilide, azimilide, flecainide, encainide, sotolol, propafenone, or other medications used to treat atrial fibrillation such as beta blockers or calcium channel blockers. The substance 12 may comprise any neuro toxic or cardio toxic agent, currently known or discovered in the future, which achieves a desired therapeutic effect when applied directly to the endocardium at sufficient concentrations, and for sufficient duration. These substances will alter the electrochemical properties of the tissue being treated without destroying or ablating the myocardial cells. The substance 12 may comprise any liquid agent for ablating myocardial tissue such as desiccated alcohol, or other substances that may induce chemical infarction or apoptosis of myocardial cells to ablate an arrhythmia impulse. The substance 12 may further comprise, or be mixed with, an anti-coagulant medication or any combination of medications necessary for safe and effective treatment.

Figure 6:
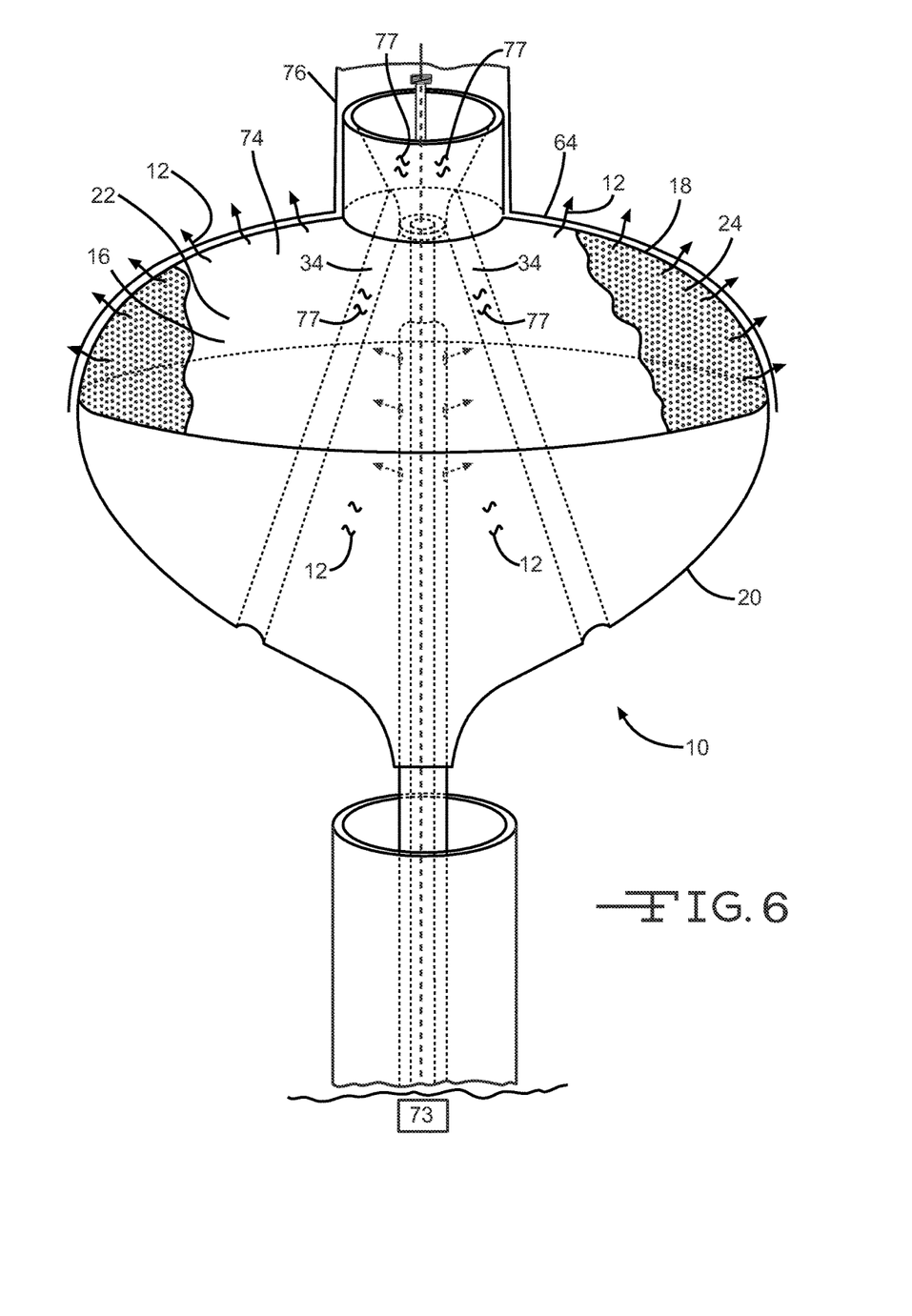
FIG. 6 illustrates the perspective view of the apparatus of FIG. 5 with a substance being infused through the apparatus into mammalian tissue.

As shown in FIG. 6, the substance 12, disposed in the cavity 22 between the flexible, absorbent, porous portion 18 of the member 16 and the non-porous portion 20 of the member 16, may then be infused, using the infusion device 73, through the flexible, absorbent, porous portion 18 to saturate the flexible, absorbent, porous portion 18 and contact the internal mammalian tissue 64, which may comprise pulmonary vein ostial tissue, pulmonary vein tissue 76, or an endocardial surface of the left atrium 74. The substance 12 may alter the physiologic properties of the internal mammalian tissue 64 to treat arrhythmia. In one embodiment, the substance 12 may ablate internal mammalian tissue 64, such as pulmonary vein ostial tissue, pulmonary vein tissue 76, or an endocardial surface of the left atrium 74, to treat arrhythmia. This may lead to substantial improvement in arrhythmia and/or in arrhythmia being completely cured. Due to the blood 77 being allowed to flow from the pulmonary vein 76 through the second lumen 34 of the balloon 24 into the left atrium 74, minimizing or eliminating the temporary reduction of blood flow from the pulmonary vein 76 into the left atrium 74 during use of the balloon 24, the substance 12 may be infused through the flexible, absorbent, porous portion 18 into contact with the internal mammalian tissue 64 for a prolonged period of time (such as a few minutes, an hour, a few hours, days, weeks, or other periods of time) at any necessary concentration to achieve the desired effect. During this time, the effect of the substance 12 on the mammalian tissue 64 may be monitored in order to achieve effective results prior to removing the substance 12 from being in contact with the mammalian tissue 64. Moreover, during this time, varied substances 12 having differing effects may be sequentially applied to tailor the treatment to the particular patient in order to achieve the desired results. In other embodiments, any number of substances 12 may be infused through the flexible, absorbent, porous portion 18 into contact with the internal mammalian tissue 64 at any concentration or duration.

Figure 7:
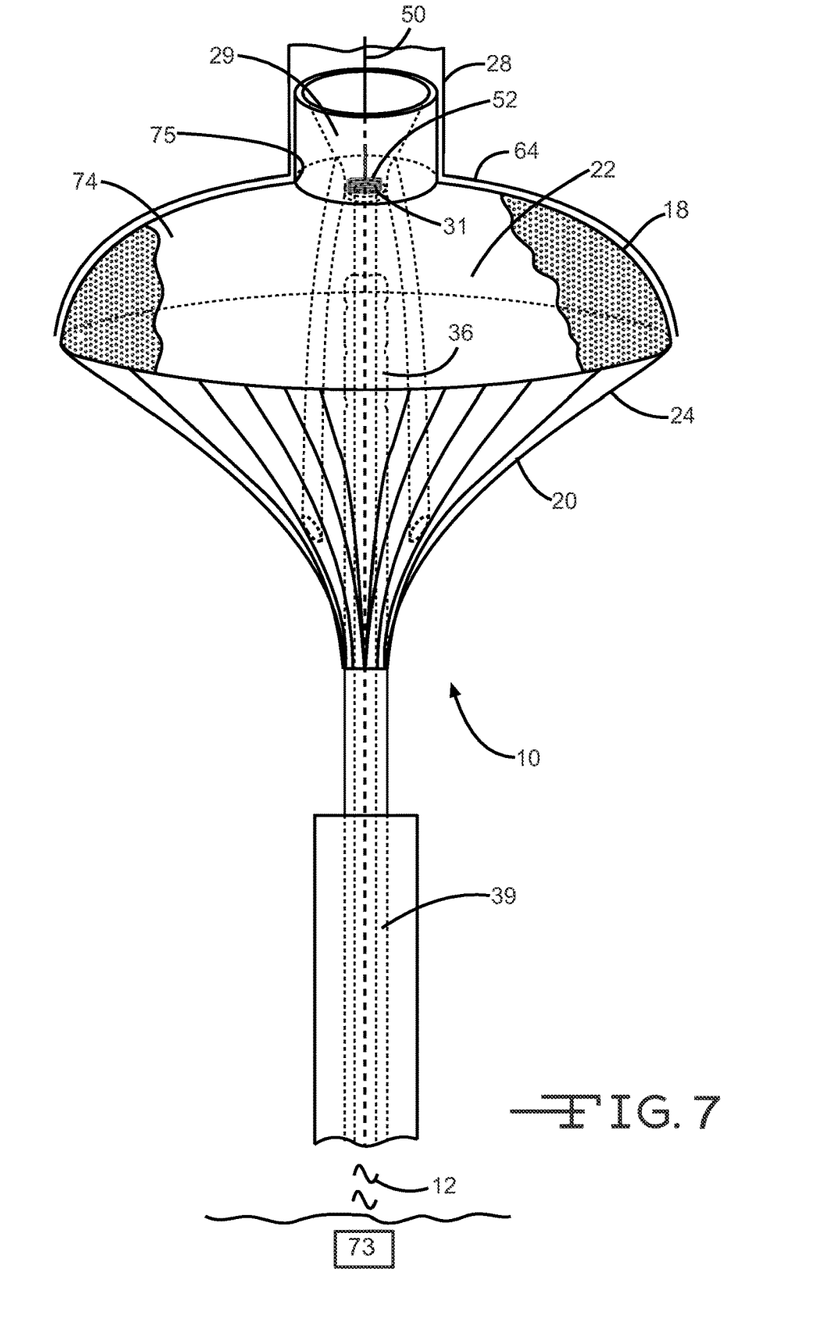
FIG. 7 illustrates a perspective view of the apparatus of FIG. 6 with the apparatus being deflated.

As shown in FIG. 7, after the mammalian tissue 64 around hole 75 of the left atrium 74 has been fully treated, the infusion device 73 may be used to apply negative pressure suction in order to vacuum the substance 12 out of the balloon 24 to put the balloon 24 back into an unexpanded state. This may be done by using the infusion device 73 to vacuum the substance 12 out of the cavity 22, through the third lumen 36, and out of the second catheter lumen 39 in order to vacuum the substance 12 out of the cavity 22 of the balloon 24. During this process, the flexible, absorbent, porous portion 18 and the non-porous portion 20 of the balloon 24 may begin to compress and crinkle as the cavity 22 is emptied of the substance 12, and the attachment clip 81 may be released. The guide-wire 50 may be moved to move the stepped-up portion 52 of the guide-wire 50 through the tapered hole 29 in the nipple 28 until it abuts against the base surface 31 of the nipple 28.

Figure 8:
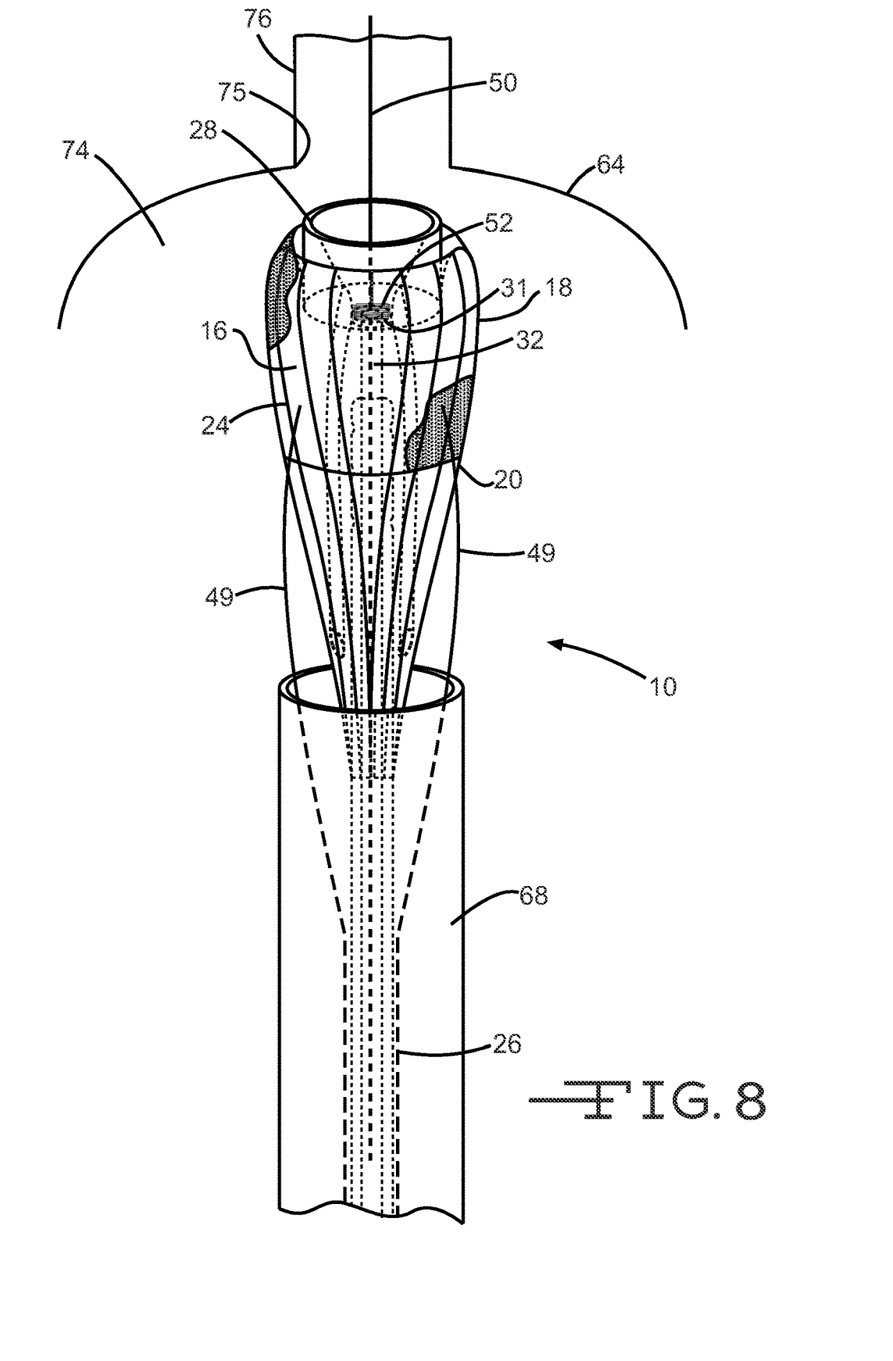
FIG. 8 illustrates a perspective view of the apparatus of FIG. 7 with the apparatus beginning to be retracted back into the sheath.
Figure 9:
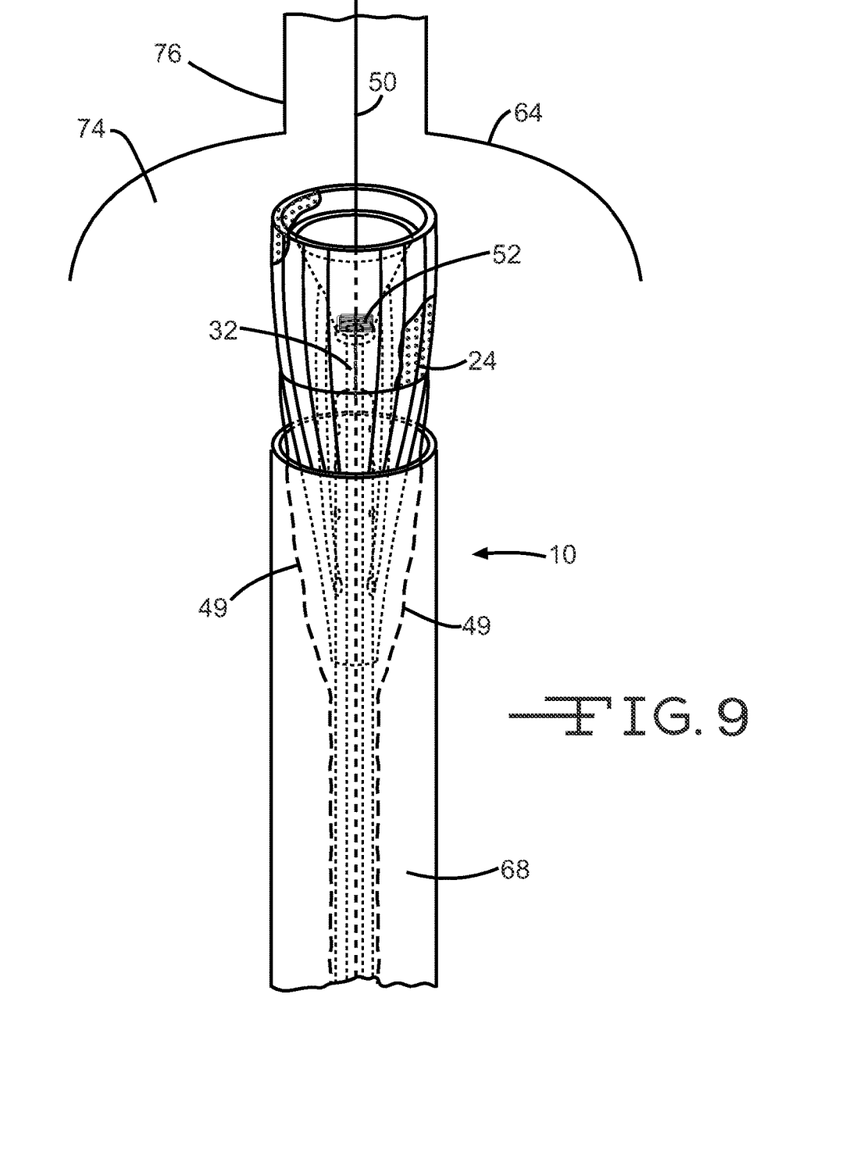
FIG. 9 illustrates a perspective view of the apparatus of FIG. 8 with the apparatus further retracted back into the sheath.
Figure 10:
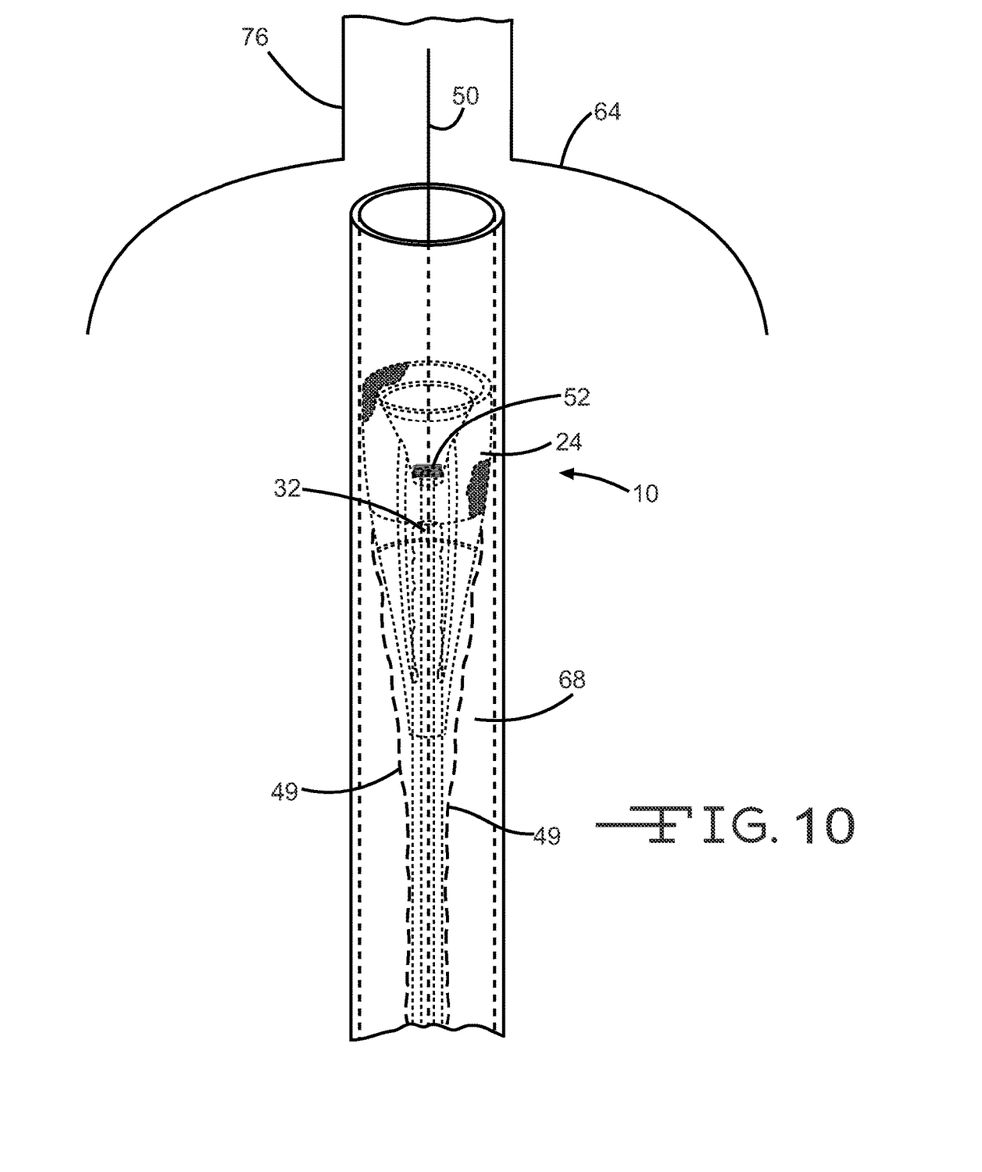
FIG. 10 illustrates a perspective view of the apparatus of FIG. 9 with the apparatus completely retracted back into the sheath.

As shown in FIG. 8, the guide-wire 50 may be moved to retract the nipple 28 of the member 16 out of the hole 75 of the left atrium 74 due to the stepped-up portion 52 of the guide-wire 50 abutting against and forcing the base surface 31 of the nipple 28 out of the hole 75. As shown in FIGS. 1 and 2, the stepped-up portion 52 of the guide-wire 50 has a wider width 54 than the width 44 of the first lumen 44. The nipple 28 of the member 16 may subsequently be inserted at separate times into other holes, comprising other pulmonary vein ostiums, of the left atrium 74. As described above with respect to hole 75, the substance 12 may be infused, using the same process, into the other holes, in order to treat the tissue around each of these holes. In such matter, the member 16 may be used to treat all internal mammalian tissue 64, comprising pulmonary vein ostial tissue, pulmonary vein tissue 76, or endocardial surfaces of the left atrium 74, which require treatment to improve or resolve arrhythmia. After all of the desired internal mammalian tissue 64 has been treated, the stepped-up portion 52 of the guide-wire 50 may be moved against the base surface 31 of the nipple 28 to force the flexible, absorbent, porous portion 18 to gradually collapse within the non-porous portion 20 of the deflated balloon 24 from the configuration of FIG. 8, to the configuration of FIG. 9, into the configuration of FIG. 10 in which it is disposed in a tulip configuration within the non-porous portion 20 of the balloon 24. As shown in FIGS. 8-10, as the stepped-up portion 52 of the guide-wire 50 is moved, the deflated balloon 24 is forced to gradually retract from the position of FIG. 8, to the position of FIG. 9, and into the position of FIG. 10 in which it is disposed completely retracted back in the stowed position within the sheath 68. The balloon 24 material is sufficiently soft and malleable to allow easy retraction back into the collapsed configuration within the sheath 68. During this process, one or more Nitinol runners 49, connected between the flexible, absorbent, porous portion 18 and the catheter 26, may be used to assist in retracting the balloon 24 back into the sheath 68. The retracted balloon 24, stowed in the unexpanded/deflated state within the sheath 68, may then be removed from the mammal along with the sheath 68. This may be accomplished by following the first lumen 32 of the balloon 24 along the guide-wire 50 in order to remove the balloon 24 and the sheath 68 from the pulmonary vein 76.

One or more embodiments of the disclosure may allow for the chemical treatment of atrial fibrillation, or other non-atrial fibrillation internal mammalian tissue issues, using a malleable, expansile, absorbent surface which consistently contacts the targeted endocardial and pulmonary vein tissue to deliver the chemical to the targeted cell tissue, without leaving gaps, and without relying on the current technique of delivering multiple ablative injury lines. This treatment allows the chemical to be narrowly applied to only the targeted tissue through a much easier and less-costly method than current treatments using standard interventional cardiology techniques which may be performed by any operator trained in catheter based cardiac procedures, as well as electrophysiologists, allowing for the treatment of patients worldwide, many of which currently lack access to treatment. This treatment may allow for the avoidance of serious side effects associated with current drug treatments as a result of eliminating the need for high dose systemic ingestion of drugs, thus avoiding side effects and toxicities. Moreover, this treatment may reduce the risk of serious side effects associated with current catheter based ablation techniques due to the use of the apparatus 10. The treatment may have the following benefits over current catheter based ablation techniques: being less-traumatic to the myocardium; not requiring focal contact of a catheter tip to atrial tissue; not requiring delivery of radiofrequency based thermal injury, or cold cryo based injury; not requiring electrical mapping of the targeted tissue; may be applied directly to each of the pulmonary vein Ostia and surrounding left atrial tissue; may allow anti-arrhythmic medications or other substances to be directly applied to the targeted tissue to interfere with the cellular membrane electrochemical properties which trigger the myocardial cell fibrillation; may allow any number of substances to be applied, together or sequentially, to the tissue for varied durations and at varied concentrations; and may allow effective treatment of the atrial fibrillation without injuring the cell function itself resulting in averting the potential for the complication of pulmonary vein stenosis, cardiac perforation, or injury related embolization.

It should be understood, of course, that the foregoing relates to exemplary embodiments of the disclosure and that modifications may be made without departing from the spirit and scope of the disclosure as set forth in the following claims.

I claim:

1. An apparatus for applying a substance to internal mammalian tissue, the apparatus comprising:
   a porous portion;
   a non-porous portion connected to the porous portion to form an inflatable and deflate-able cavity between the porous portion and the non-porous portion;
   a first lumen at least partially positioned in the cavity and configured to communicate the substance to the cavity;
   a nipple;
   a second lumen extending from a lateral surface of one of the porous portion and the non-porous portion into the nipple; and
   a third lumen extending into the nipple.

2. The apparatus of claim 1, further comprising a fourth lumen extending from a lateral surface of the one of the porous portion and the non-porous portion and into the nipple.

3. The apparatus of claim 2, wherein the second and fourth lumens extend from the non-porous portion into the nipple.

4. The apparatus of claim 3, wherein the second and fourth lumens extend through the cavity.

5. The apparatus of claim 4, wherein the second and fourth lumens are not in fluid communication with the cavity.

6. The apparatus of claim 2, wherein the second and fourth lumens are crescent shaped.

7. The apparatus of claim 2, wherein the cavity formed by the porous portion and the non-porous portion includes a first end and a second end opposite the first end, wherein the nipple is positioned near the first end of the cavity, wherein the second and forth lumens each include a first end and a second end, wherein the first ends of the second and forth lumens are in fluid communication with and open into the nipple and the second ends of the second and forth lumens are positioned near the second end of the cavity.

8. The apparatus of claim 1, wherein the second lumen extends from the non-porous portion into the nipple.

9. The apparatus of claim 8, wherein the second lumen extends through the cavity.

10. The apparatus of claim 9, wherein the second lumen is not in fluid communication with the cavity.

11. The apparatus of claim 1, further comprising a guide-wire configured to be positioned in the third lumen.

12. The apparatus of claim 11, wherein the guide-wire includes a first portion and as second portion, wherein the first portion of the guide-wire has a first width greater than a second width of the second portion, and wherein the width of the first portion is greater than a width of the third lumen.

13. The apparatus of claim 1, wherein the second and third lumens are open-ended.

14. The apparatus of claim 1, wherein the second lumen is crescent shaped.

15. The apparatus of claim 1, wherein the cavity formed by the porous portion and the non-porous portion includes a first end and a second end opposite the first end, wherein the nipple is positioned near the first end of the cavity, wherein the second lumen includes a first end and a second end, wherein the first end of the second lumen is in fluid communication with and opens into the nipple and the second end of the second lumen is positioned near the second end of the cavity.

16. An apparatus for applying a substance to internal mammalian tissue, the apparatus comprising:
   a porous portion;
   a non-porous portion connected to the porous portion to form an inflatable and deflate-able cavity between the porous portion and the non-porous portion;
   a lumen at least partially positioned in the cavity and configured to communicate the substance to the cavity;
   a nipple;
   a guide-wire;
   a ferromagnetic portion; and
   a magnetic member;
   wherein one of the ferromagnetic portion and the magnetic member is positioned in the nipple and the other of the ferromagnetic portion and the magnetic member is coupled to the guide wire, and wherein the ferromagnetic portion is at least one of attracted to or repulsed by the magnetic member.

17. The apparatus of claim 16, wherein the lumen extends through a long axis of the cavity.

18. The apparatus of claim 16, wherein the lumen is a first lumen, the apparatus further comprising a second lumen, wherein a width of the magnetic member is greater than a width of the second lumen.

19. The apparatus of claim 18, wherein the first and second lumens extend along a long axis of the cavity.

20. The apparatus of claim 19, wherein the guide-wire is configured to be at least partially positioned in the second lumen.

21. The apparatus of claim 16, wherein the magnetic member is an electromagnet.

22. The apparatus of claim 21, wherein the magnetic member is adjustable to adjust a strength of the at least one of the attraction or repulsion of the magnetic member.

23. The apparatus of claim 16, wherein the ferromagnetic portion is positioned in the nipple and the magnetic member is coupled to the guide wire.

24. The apparatus of claim 16, wherein the magnetic member has a first width and a portion of the guide-wire has a portion with a second width less than the first width.

25. The apparatus of claim 16, wherein the lumen is aligned with and attached to a catheter.

26. The apparatus of claim 16, wherein the lumen is a first lumen, the apparatus further comprising a second lumen extending from a lateral surface of one of the porous portion and the non-porous portion.

27. The apparatus of claim 16, wherein the lumen is a first lumen, the apparatus further comprises a second lumen and a third lumen, wherein the second and third lumens are open-ended.

28. The apparatus of claim 16, wherein the nipple extends from the porous portion, the apparatus further comprising a second lumen that extends into the nipple.

29. The apparatus of claim 16, wherein the nipple includes a base surface and the ferromagnetic portion is in the base surface of the nipple.

* * * * *